United States Patent
Gehrig

(10) Patent No.: US 8,957,688 B2
(45) Date of Patent: Feb. 17, 2015

(54) DETERMINING A DIELECTRIC PROPERTY OF A CAPACITOR

(75) Inventor: Reto Gehrig, Winterhur (CH)

(73) Assignee: Uster Technologies, AG, Uster (CH)

( * ) Notice: Subject to any disclaimer, the term of this patent is extended or adjusted under 35 U.S.C. 154(b) by 664 days.

(21) Appl. No.: 13/121,583

(22) PCT Filed: Oct. 12, 2009

(86) PCT No.: PCT/CH2009/000328
§ 371 (c)(1),
(2), (4) Date: Mar. 29, 2011

(87) PCT Pub. No.: WO2010/043064
PCT Pub. Date: Apr. 22, 2010

(65) Prior Publication Data
US 2011/0193572 A1 Aug. 11, 2011

(30) Foreign Application Priority Data
Oct. 16, 2008 (CH) ........................................ 1645/08

(51) Int. Cl.
*G01R 27/26* (2006.01)
*G01N 33/36* (2006.01)
(Continued)

(52) U.S. Cl.
CPC ............ *G01N 33/365* (2013.01); *B65H 63/064* (2013.01); *G01R 27/2623* (2013.01); *G01N 27/228* (2013.01)
USPC ............. 324/681; 324/663; 324/674; 73/159; 73/160

(58) Field of Classification Search
CPC .................................................... G01N 27/228
See application file for complete search history.

(56) References Cited

U.S. PATENT DOCUMENTS

| 3,864,626 A | 2/1975 | McClean |
| 3,986,108 A | 10/1976 | Thomas |

(Continued)

FOREIGN PATENT DOCUMENTS

| EP | 0922963 | 6/1999 |
| GB | 638365 | 6/1950 |

(Continued)

OTHER PUBLICATIONS

Machine English translation of Japanese Patent Application Publication to Inventor Miyagawa Tatsuo. JP 2002-005971 A, Jan. 9, 2002. Translation of pp. 2-8 created on Jun. 1, 2013.*
Machine English translation of International Patent Application Publication to Inventors Philipp Ott and Peter Schmid. WO 2006/105676 A1, Oct. 12, 2006. Translation of pp. 1-18 created on Jul. 22, 2014.*

(Continued)

*Primary Examiner* — Melissa Koval
*Assistant Examiner* — Steven G Armstrong
(74) *Attorney, Agent, or Firm* — Luedeka Neely Group, P.C.; Rick Barnes

(57) ABSTRACT

An apparatus for determining at least one dielectric property of a capacitor arrangement, and especially for capacitive examination of a moving elongated test subject such as yarn. It contains an alternating signal generator for applying an electric alternating signal to the capacitor arrangement. The capacitor arrangement is uncoupled from the alternating signal generator by means of an amplifier in such a way that it does not relevantly influence the basic frequency and the signal shape of the applied alternating signal. Detection means detect an electric measuring variable of an electric signal tapped from the capacitor arrangement. The alternating signal generator is set up in such a way that at least one of the basic frequency and the signal shape of the applied alternating signal can be changed.

9 Claims, 2 Drawing Sheets

(51) Int. Cl.
*B65H 63/06* (2006.01)
*G01N 27/22* (2006.01)

(56) References Cited

U.S. PATENT DOCUMENTS

| | | | |
|---|---|---|---|
| 4,843,879 A | | 7/1989 | Enderlin |
| 6,346,819 B1 | | 2/2002 | Joss |
| 6,369,588 B1 | | 4/2002 | Sleefe |
| 6,476,619 B1 | * | 11/2002 | Moshe et al. .............. 324/634 |
| 7,659,730 B2 | * | 2/2010 | Schroder .................... 324/658 |
| 2008/0111563 A1 | | 5/2008 | Ott |

FOREIGN PATENT DOCUMENTS

| | | |
|---|---|---|
| GB | 1499632 | 2/1978 |
| JP | 2002005971 | 1/2002 |
| WO | WO 2006105676 A1 * | 10/2006 |
| WO | 2007115416 | 10/2007 |

OTHER PUBLICATIONS

Hewlett-Packard XP002563591, retrieved from the Internet: http://www.hparchive.com/catalogs/hp-catalog-1966-1967.pdf, p. 30.

* cited by examiner

DETERMINING A DIELECTRIC PROPERTY OF A CAPACITOR

FIELD OF THE INVENTION

The present invention lies in the field of the examination of substances by electric means. It relates to an apparatus and a method for determining at least one dielectric property of a capacitor arrangement according to the preambles of the independent claims.

A preferred field of application for the invention is the capacitive testing of elongated, preferably textile structures such as card slivers, roving, yarns or fabrics. The invention thus also relates to an apparatus for the capacitive examination of a moved elongated test subject according to the preamble of a further claim. The goal of such an examination can be for example the detection of foreign substances, the recognition of changes of the mass per unit of length and/or the measurement of humidity in the test subject. The invention can be used for example in the production process (online) in yarn cleaners in spinning and bobbing winding machines or in laboratory tests (offline) in yarn testing devices.

BACKGROUND

A large number of various apparatuses are known for examining or testing elongated textile test subjects such as card slivers, roving, yarns or fabrics for example. Depending on their application, they can be categorized into the two classes of laboratory test (offline) and testing during the production process (online). The apparatuses make use of the various known sensor principles, of which the capacitive measuring principle is of special interest in this case, wherein a measuring capacitor is typically arranged as a planar plate capacitor and comprises a through-opening for the test subject. The measuring capacitor is part of an LC oscillator, so that an electric alternating voltage is applied to the measuring capacitor upon excitation of the LC oscillator. The through-opening is thus subjected to an alternating electrical field. The test subject is moved through the plate capacitor and is subjected to the alternating field. An electric output signal of the plate capacitor is detected. Dielectric properties of the test subject are determined from the output signal in an evaluation circuit. Changes in the parameters of the test subject such as mass per unit of length and/or material composition are determined from the dielectric properties. A capacitive yarn or sliver sensor is described for example in GB-638,365 A.

In order to enable the performance of precise measurements which are not influenced by external influences such as air temperature or air humidity, a compensation method is frequently applied. For this purpose, the apparatus comprises a reference capacitor in addition to the actual measuring capacitor. It can be formed by adding a third capacitor plate arranged parallel to the two measuring capacitor plates, with the three capacitor plates being switched together into one capacitive measuring circuit. Examples for measuring circuits and suitable evaluation circuits for their output signals can be found in the specifications EP-0,924,513 A1, WO-2006/105676 A1 and WO-2007/115416 A1.

A device for the capacitive quality control of textile threads is known from U.S. Pat. No. 4,843,879 A. It contains a double-capacitor arrangement with a measuring capacitor and a reference capacitor. The double-capacitor arrangement is built into an electric circuit. The circuit contains an oscillator for applying two alternating voltages with opposite phases to the two outer capacitor electrodes of the double-capacitor arrangement. A signal amplifier and a balancing capacitor are disposed in each branch between the oscillator and the respective electrode, with which the output signal of the double-capacitor arrangement can be balanced to the value of zero without any test subject.

WO-2006/069720 A2 discloses a measuring apparatus and a measuring method for the capacitive recognition of foreign bodies in a product, especially in tobacco, cotton or any other fiber product. A high-frequency generation device generates a high-frequency wave which is applied to the measuring capacitor. The voltage amplitude of the generated high-frequency wave is kept constant by means of a closed-loop control device.

An evaluation circuit for determining complex impedances is known from EP-0,922,963 A2. A voltage source generates two alternating voltage signals, of which one is applied to the impedance to be measured. The output signal of the impedance is combined with the other alternating voltage signal which is phase-shifted by 0° or 90° respectively in such a way that the real part and the imaginary part of the impedance can be determined from the respectively resulting output signals. The voltage source comprises a frequency generator for generating digital signals, a 1:2 frequency divider and a D-flip-flop for generating two alternating voltage signals phase-shifted by 90°. The phase shifting is maintained in the variation of the frequency.

JP-2002-005971 A shows an apparatus for capacitive differentiation of various fluids such as distilled water and tap water and for the detection of non-metallic foreign substances in fluids. For this purpose a circuit in which a sample is disposed is scanned in a broadband manner and the dispersion is determined. A direct digital synthesizer (DDS) is used as a signal generator for the scanning.

In the case of the capacitive sensors known from the state of the art, the measuring capacitor or measuring circuit is part of an LC oscillator. The measuring capacitor thus influences parameters of the alternating voltage applied to the same such as its frequency, phase and amplitude. On the other hand, an LC oscillator usually has a single resonant frequency, or at least a very limited number of discrete resonant frequencies, on which it can be operated. The resonant frequency and the phase can only be changed or balanced with a lot of effort.

SUMMARY

It is therefore an object of the present invention to provide an apparatus and a method for determining at least one dielectric property of a capacitor arrangement which does not have the disadvantages as outlined above. The apparatus and the method shall be applicable in an especially more flexible way and shall be better controllable than the state of the art. They shall offer the possibility to examine the capacitor arrangement in various respects and/or with respect to various properties and to thus characterize the same better and more completely. It is a further object of the invention to provide an apparatus and a method for the capacitive examination of a moved elongated textile test subject such as card sliver, roving, yarn or fabric, with which the test subject can be characterized better and more completely. In particular, parameters of the textile test subject such as the presence, type and percentages of foreign substances, changes in mass per unit of length or humidity should be determined in a reliable manner and be distinguished from one another.

These and other objects are achieved by the apparatuses in accordance with the invention and the methods in accordance with the invention, as defined in the independent claims. Advantageous embodiments are stated in the dependent claims.

The invention is based on the idea to uncouple the capacitor arrangement from an alternating signal generator driving the same in such a way that it does not relevantly influence the parameters of the electrical alternating signal generated by the alternating signal generator, especially a basic frequency and signal shape of the alternating signal. The alternating signal generator and the capacitor arrangement are thus components that are independent from each other. In particular, the capacitor arrangement is no longer part of the alternating signal generator. The alternating signal generator allows generating an alternating signal with virtually random parameters, especially the basic frequency and signal shape, and applying the signal to the capacitor arrangement.

The term "capacitor arrangement" shall be understood in this specification as being an arrangement with two bodies which can be charged in a non-similar manner by the electrical alternating signal of the alternating signal generator and are separated from one another by at least one dielectric. In a preferred embodiment, the capacitor arrangement concerns a capacitor with two mutually spaced plates, between which air is disposed and between which a moved elongated textile test subject can be inserted which is to be examined. The term "electrical alternating signal" shall be understood within this specification to be an electric voltage or current signal with at least one time-varying, preferably periodic, component (AC component), which can additionally be superposed by a temporally substantially constant component (DC component, offset). The periodic component has a specific basic frequency and a specific signal shape. The "basic frequency" is the lowest frequency which occurs in the frequency spectrum of the alternating signal. Examples for signal shapes are sinus, triangle, saw-tooth, rectangular, etc., with the respective basic pattern repeating periodically with the basic frequency. The demand according to which the capacitor arrangement will influence the parameters of the electrical alternating signal in a "non-relevant" manner requires that the capacitor arrangement is in any case not a frequency-determining part of the measuring oscillating circuit. Resonant components of the alternating signal which are caused by the capacitor arrangement are not excluded.

The apparatus in accordance with the invention for determining at least one dielectric property of a capacitor arrangement contains at least one alternating signal generator for applying an electrical alternating signal with a specific basic frequency and a specific signal shape to the capacitor arrangement. The capacitor arrangement is uncoupled from the at least one alternating signal generator in such a way that it does not relevantly influence the basic frequency and the signal shape of the applied alternating signal. The apparatus further comprises detection means for detecting at least one electric measuring variable of alternating signal tapped from the capacitor arrangement. The at least one alternating signal generator is arranged in such a way that the basic frequency and/or the signal shape of the applied alternating signal can be modified.

The at least one alternating signal generator is preferably arranged in such a way that a phase position and/or an amplitude of the alternating signal generated by said generator can additionally be predetermined. For the purpose of uncoupling, the at least one alternating signal generator is provided with at least one amplifier in series connection for amplifying the alternating signal generated by the alternating signal generator. A filter for filtering the alternating signal generated by the alternating signal generator can be connected in series with the at least one alternating signal generator.

The at least one alternating signal generator is preferably chosen from the following group: RC oscillator, LC oscillator, quartz oscillator, oscillator with ceramic resonator, oscillator with SAW component (surface acoustic waves, SAW), oscillator with logic units, synthesizer, phase-locked loop (PLL), pulse-width modulator (PWM), trigger circuit.

A synthesizer is used as an alternating signal generator in a preferred embodiment. The term "synthesizer" shall be understood in this specification as a mixed-signal (digital and analog) electronic apparatus for generating analog electric alternating voltage signals. Direct digital synthesizers (DDS) are used especially advantageously in the apparatus in accordance with the invention. A DDS is an electronic component which is principally capable of generating analog signals of any signal shape, frequency and/or phase position, with individual types being subject to certain limitations. It has a digital hardware that is operated with a fixed frequency (clock frequency). Digital values of an entire or half period of a periodic signal such as a sine signal are stored as a table in a computer memory (programmable read-only memory, PROM) of the DDS. These supporting points are retrieved during signal generation. Certain supporting points can be omitted or doubled, so that random frequencies can be generated.

Several alternating signal generators are present in a preferred embodiment, and control means for controlling the alternating signal generator are arranged in such a way that phases of alternating voltage signals of different alternating signal generators can be phase-shifted against each other by predetermined phase differences.

The apparatus in accordance with the invention can contain a reference capacitor which is connected in series to the capacitance to be measured.

The apparatus in accordance with the invention is preferably used for the capacitive examination of a moved elongated textile test subject such as card sliver, roving yarn, yarn or fabric, with the moved test subject influencing the capacitance to be measured.

A further subject matter of the present invention is an apparatus for the capacitive examination of a moved elongated, preferably textile test subject such as card sliver, roving yarn, yarn or fabric. It contains a capacitive measuring circuit with a measuring capacitor for receiving the test subject and at least one electric alternating signal generator for applying an electric alternating signal with a specific basic frequency and a specific signal shape to the measuring capacitor. The capacitive measuring circuit is uncoupled from the at least one alternating signal generator in such a way that it does not relevantly influence the basic frequency and the signal shape of the applied alternating signal. The apparatus further comprises detection means for the detection of at least one electric measuring variable of an electric signal tapped from the measuring capacitor. The at least one alternating signal generator is arranged in such a way that the basic frequency and/or the signal shape of the applied alternating signal can be changed.

In the method in accordance with the invention for determining at least one dielectric property of a capacitor arrangement, an electric alternating signal with a specific basic frequency and a specific signal shape is generated by at least one alternating signal generator and applied to the capacitor arrangement. The capacitor arrangement is uncoupled from the alternating signal generator in such a way that it does not relevantly influence the basic frequency and the signal shape of the applied alternating signal. At least one electric measuring variable of an electric signal tapped from the capacitor arrangement is detected. The basic frequency and/or the signal shape of the applied alternating signal are changed. Preferably, a phase position and/or an amplitude of the alternating signal are additionally changed. It is possible to generate several alternating signals, with their mutual phases being phase-shifted by predetermined phase differences against one another.

In the method in accordance with the invention for the capacitive examination of a moved elongated, preferably textile test subject such card sliver, roving yarn, yarn or fabric, the test subject is introduced into a measuring capacitor. An electric alternating signal with a specific basic frequency and specific signal shape is generated by at least one alternating signal generator and is applied to the measuring capacitor. The measuring capacitor is uncoupled from the at least one alternating signal generator in such a way that it does not relevantly influence the basic frequency and the signal shape of the applied alternating signal. At least one electric measuring variable of an electric signal applied to the measuring capacitor is detected. The basic frequency and/or the signal shape of the applied alternating signal are changed.

As a result of the invention, the alternating signal applied to the capacitor arrangement can be set with respect to its basic frequency and/or the signal shape in a simple way and with high precision. It can thus be adjusted optimally to the respective test subject, the chosen measuring method and/or the prevailing ambient conditions. The invention even opens up possibilities for entirely new measuring methods such as measurements with frequency and phase modulation, changing mutual phase positions, etc. Several parameters of the test subject can accordingly be determined from measurements with at least two alternating signals with defined mutual phase positions, e.g. the mass, the humidity content and the composition of the material (or the content of foreign substances) of the test subject. Methods for evaluating measuring signals from such measurements are known for example from EP-0,924,513 A1 and WO-2007/115416 A1.

BRIEF DESCRIPTION OF THE DRAWINGS

The invention is explained below in closer detail by reference to the schematic drawings.

DETAILED DESCRIPTION

The preferred embodiments of the invention as discussed below use at least one synthesizer as an alternating signal generator. This shall be not understood in a limiting manner. It is understood that many other alternating signal generators known to the person skilled in the art can be used in the invention.

Figure 1:
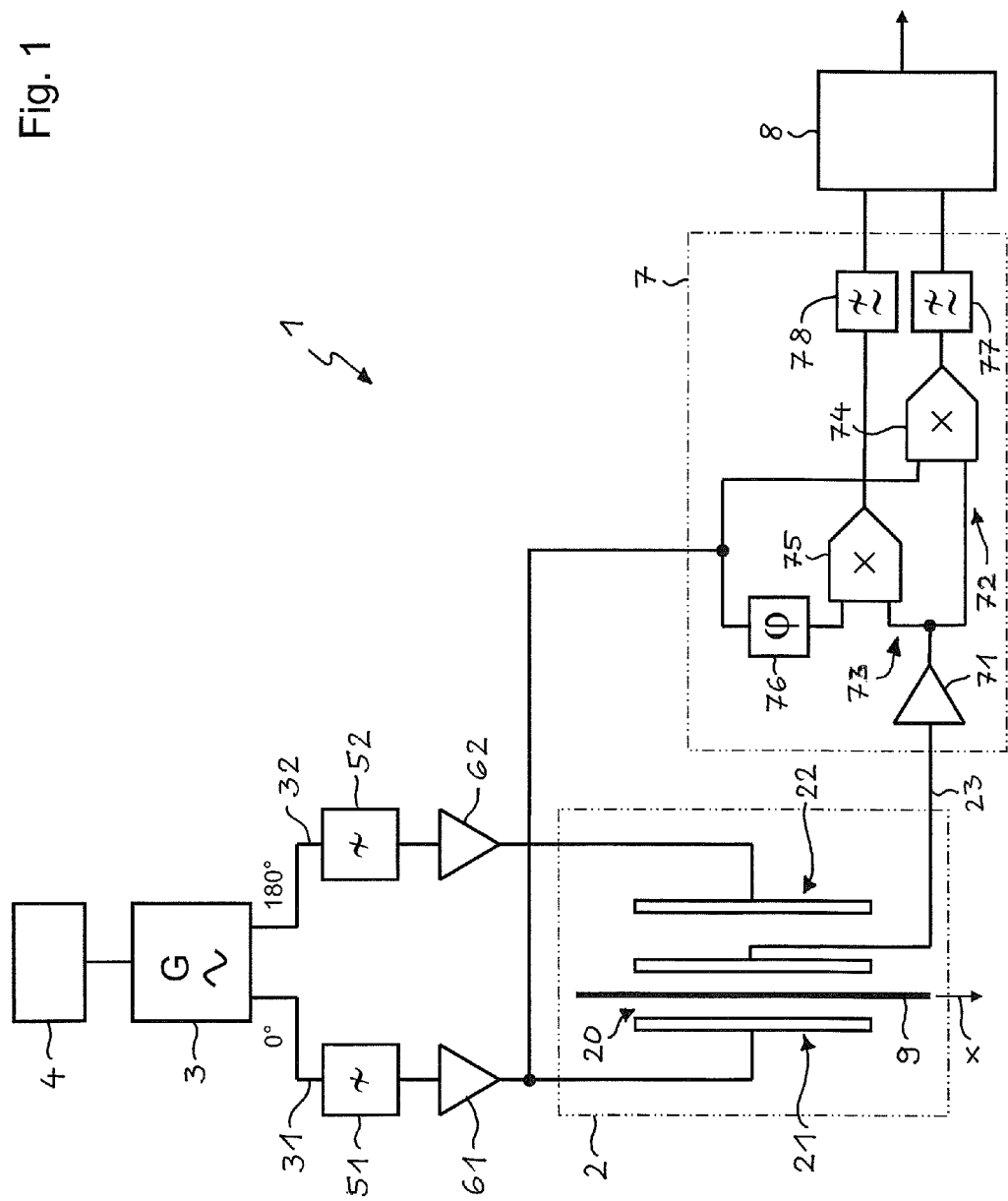
FIGS. 1 and 2 show circuit diagrams for two embodiments of the apparatus in accordance with the invention.

FIG. 1 shows an electric circuit diagram of a first embodiment of the apparatus 1 in accordance with the invention. Apparatus 1 contains a measuring circuit 2 with a measuring capacitor 21 for an elongated test subject 9 or yarn which is moved along its longitudinal direction x. The measuring capacitor 21 comprises two parallel capacitor plates and an interposed through-opening 20 for the test subject 9. Optionally, a reference capacitor 22 is present in the measuring circuit 2 for increasing the measuring precision and for eliminating or reducing undesirable ambient influences such as air humidity or air temperature. The reference capacitor 22 is preferably arranged in the same manner as the measuring capacitor 21, with the difference that it is not passed through by the test subject 9. The measuring capacitor 21 and the reference capacitor 22 are connected in series with respect to each other and jointly form a capacitive voltage divider. It is understood that the measuring circuit 2 can contain further components that are not shown here.

Apparatus 1 further contains an electric alternating voltage generator 3 arranged as a synthesizer for example for generating an alternating voltage signal which is applied to the measuring circuit 2. This subjects the through-opening 20 of the measuring capacitor 21 to an electric alternating field which interacts with the test subject 9. Accordingly, it is possible to draw conclusions on the properties of the test subject 9 from an output signal of the measuring capacitor 21. The reference capacitor 22 is also subjected to an alternating electric field.

A direct digital synthesizer (DDS) is used in a preferred embodiment as a synthesizer 3. The DDS can be controlled by a digital interface 4.

FIG. 1 shows an embodiment in which the synthesizer 3 generates an alternating voltage signal such as a sinusoidal signal of a specific frequency. Signal components with frequencies other than the basic frequency can also occur. Frequencies from the range of between 1 MHz and 100 MHz, preferably between 5 MHz and 50 MHz, and approximately equal to 10 MHz for example, are especially suitable for examining yarn 9 and other elongated textile structures. Synthesizer 3 preferably comprises two output lines 31, 32, with a first signal being output on a first output line 31 and a second signal on a second output line 32 which is substantially identical to the first signal, but is phase-shifted in relation to the same by 180°.

The two signals generated by the synthesizer 3 can optionally be filtered by respective filters 51, 52. They are then respectively amplified by one amplifier 61, 62, e.g. an operational amplifier. The signals thus amplified are supplied to the measuring circuit 2. Although the measuring circuit 2 thus receives alternating voltage signals generated by the synthesizer 3, it is uncoupled from the synthesizer 3 by the amplifiers 61, 62 in such a way that it does not influence the parameters of the alternating voltage signals generated by the synthesizer 3.

The measuring circuit 2 is preferably connected with a demodulator 7 for an output signal of the measuring circuit 2 arriving on an electric line 23. The demodulator 7 is used for the demodulation of the analog output signal of the measuring circuit 2, i.e. the analog conditioning and extraction of a low-frequency signal from the electric signal tapped from the measuring circuit 2. In the embodiment of FIG. 1, the demodulator 7 comprises an amplifier 71 at first for amplifying the output signal. The output signal of the amplifier 71 is divided into two partial paths 72, 73 and demodulated in two different phases. The demodulation is performed substantially synchronously, as a multiplication of the partial signal components with the alternating voltage signal applied to the measuring capacitor 21 by means of multipliers 74, 75. The phase shifting in a partial path 73 is introduced by a phase shifter 76. It is preferably 90° in order to obtain a quadrature signal. It is also possible to choose another phase shifting. For smoothing, both signals are each sent through a low-pass filter 77, 78 and then supplied to an evaluation unit 8. The evaluation unit 8 can contain an analog electric circuit or a digital circuit with a processor.

Already the embodiment of FIG. 1, in which the synthesizer 3 supplies a mono-frequency alternating voltage signal, offers considerable advantages over conventional apparatuses in which the measuring circuit is a part of the alternating voltage source. The frequency of the alternating voltage signal is free within a very large range which is limited by the synthesizer 3 itself and can be set with high precision.

However, the invention offers many more freedoms regarding the alternating voltage signal. The signal supplied by the synthesizer 3 to the measuring circuit 2 can contain several signal components with different frequencies. It can be advantageous to provide a low-frequency component with a frequency from the range of between 10 KHz and 1000 KHz, preferably 50 KHz and 500 KHz and approximately equal to 200 KHz for example, in addition to a high-frequency component in the MHz range. It is also not necessary to use sinusoidal signal components. It is known however that every periodic signal can be broken down into sinusoidal components by Fourier expansion.

In summary, synthesizer 3 can mix any random number of signal components into an alternating voltage signal, with the signal shapes, frequencies, amplitudes and mutual phase positions of the various components being freely choosable.

Figure 2:
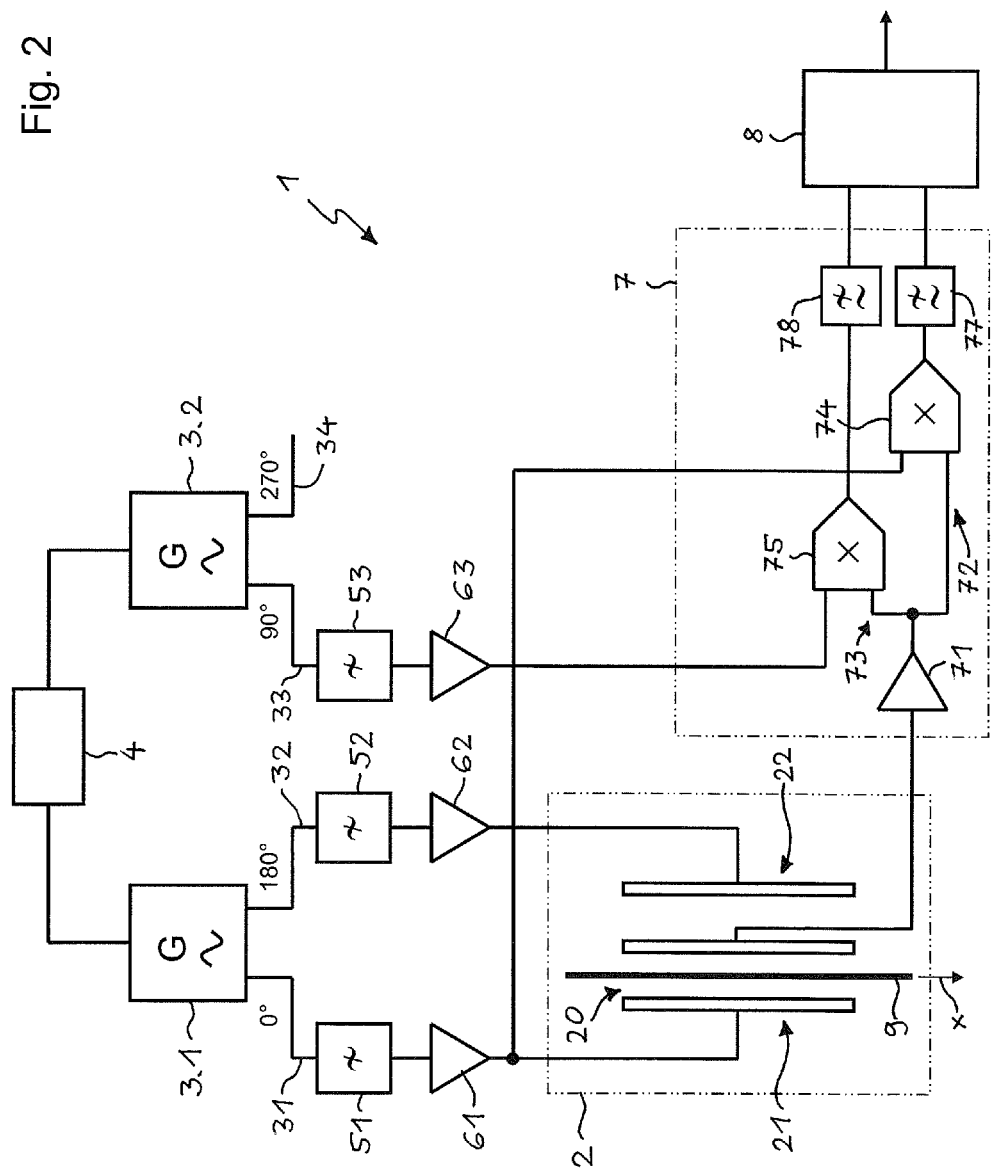

FIG. 2 shows a circuit diagram of a second embodiment of the apparatus 1 in accordance with the invention. Two mono-frequency alternating voltage signals are generated in this case which are shifted against each other by a predetermined phase difference. This is achieved with two synthesizers 3.1, 3.2, preferably DDS, which are advantageously controlled by a single digital interface 4. The digital interface 4 coordinates the two synthesizers 3.1, 3.2 in such a way that the desired phase shifting is achieved. The phase-shifted signal of the second synthesizer 3.2 is output to an output line 33 and used for demodulation of the output signal of the measuring circuit 2, in analogy to the embodiment of FIG. 1 where, for this purpose, the phase shifter 76 was used in the demodulator 7 (see FIG. 1). The phase shifting is preferably 90°, thus providing a quadrature signal. It could also assume other values or be changed. In analogy to the first synthesizer 3.1, a filter 53 or an amplifier 63 can be used for filtering and amplifying the phase-shifted signal of the second synthesizer 3.2. In the embodiment of FIG. 2, the second output 34 of the second synthesizer 3.2 remains unused, which second synthesizer 3.2 is shifted by 180° against the first output 33 and thus by 270° against the first output 31 of the first synthesizer 3.1. It could also be used for evaluating the output signal of the measuring circuit 2. As an alternative to the embodiment with two synthesizers 3.1, 3.2, the various phase-shifted signals could also be provided by one single synthesizer with respective outputs.

It is also possible to use more than two phase-shifted signals for evaluation which are provided by one single or several synthesizers. Several properties of the test subject 9 can thus be determined, e.g. the mass of the test subject 9, the humidity contained in the test subject 9 and optionally foreign substances such as polypropylene contained in the test subject 9. Moreover, it is possible with many such signals to determine the mixture ratio of various types of raw cotton of which the test subject is composed.

It is understood that the present invention is not limited to the embodiments discussed above. With the knowledge of the invention, the person skilled in the art will be able to derive further variants which also belong to the subject matter of the present invention. In particular, various known electric alternating signal generators can be used.

LIST OF REFERENCE NUMERALS

1 Apparatus
2 Measuring circuit
20 Through opening
21 Measuring capacitor
22 Reference capacitor
3 Alternating signal generator
31, 32 Output lines of the alternating signal generator
33, 34 Output lines of a second alternating signal generator
4 Digital interface
51-53 Filter
61-63 Amplifier
7 Demodulator
71 Amplifier
72, 73 Partial paths of the demodulator
74, 75 Multiplier
76 Phase shifter
77, 78 Low-pass filter
8 Evaluation circuit
9 Test subject
x Longitudinal direction of the test subject

The invention claimed is:

1. An apparatus for the capacitive examination of a moving elongated test subject, comprising:
a capacitive measuring circuit having a measuring capacitor for receiving the test subject and a reference capacitor that is not passed-through by the test subject,
the measuring capacitor and the reference capacitor connected in series with respect to each other and jointly forming a capacitive voltage divider,
an electric alternating signal generator for applying a first electric alternating signal with a specific basic frequency and a specific signal shape to the measuring capacitor, and for applying a second electric alternating signal that is substantially identical to the first electric alternating signal but is phase-shifted in relation to the first electric alternating signal by 180° to the reference capacitor,
the capacitive measuring circuit uncoupled from the alternating signal generator such that the capacitive measuring circuit does not significantly affect the basic frequency and the signal shape of the applied alternating signals, and
detection means for detecting at least one electric measuring variable of an electric signal tapped from the measuring capacitor,
the alternating signal generator configured so that at least one of the basic frequency and the signal shape of the applied alternating signals are changeable, and at least one of the phase position and the amplitude of the applied alternating signals are changeable.

2. An apparatus according to claim 1, wherein the alternating signal generator is arranged in such a way that in addition at least one of a phase position and an amplitude of the alternating signal generated thereby are predeterminable.

3. An apparatus according to claim 1, further comprising at least one filter for filtering the alternating signals generated by the alternating signal generator, and connected in series with the alternating signal generator.

4. An apparatus according to claim 1, wherein the alternating signal generator comprises at least one of an RC oscillator, LC oscillator, quartz oscillator, oscillator with ceramic resonator, oscillator with SAW component, oscillator with logic units, synthesizer, phase-locked loop, pulse-width modulator, and trigger circuit.

5. An apparatus according to claim 4, wherein the alternating signal generator is a direct digital synthesizer.

6. An apparatus according to claim 1, wherein the detection means comprise a demodulator with a multiplier connected in series with the capacitor arrangement for multiplying the electric signal tapped from the measuring capacitor with an alternating signal of the alternating signal generator.

7. An apparatus for the capacitive examination of a moving elongated test subject, comprising:

a capacitive measuring circuit having a measuring capacitor for receiving the test subject and a reference capacitor that is not passed-through by the test subject, the measuring capacitor and the reference capacitor connected in series with respect to each other and jointly forming a capacitive voltage divider, an electric alternating signal generator for applying a first electric alternating signal with a specific basic frequency and a specific signal shape to the measuring capacitor, and for applying a second electric alternating signal that is substantially identical to the first electric alternating signal but is phase-shifted in relation to the first electric alternating signal by 180° to the reference capacitor, the capacitive measuring circuit uncoupled from the alternating signal generator such that the capacitive measuring circuit does not significantly affect the basic frequency and the signal shape of the applied alternating signals, and detection means for detecting at least one electric measuring variable of an electric signal tapped from the measuring capacitor, the alternating signal generator configured so that at least one of the basic frequency and the signal shape of the applied alternating signals are changeable, wherein several alternating signal generators are present, and further comprising control means for controlling the alternating signal generators arranged in such a way that phases of alternating signals of different alternating signal generators are phase-shiftable against one another by predetermined phase differences.

8. A method for the capacitive examination of a moving elongated test subject, comprising:

introducing the test subject into a measuring capacitor, generating a first electric alternating signal with a specific basic frequency and a specific signal shape by an alternating signal generator, applying the first electric alternating signal to the measuring capacitor, generating a second electric alternating signal that is substantially identical to the first electric alternating signal, but is phase-shifted in relation to the first electric alternating signal by 180° by the alternating signal generator, applying the second electric alternating signal to a reference capacitor that is not passed through by the test subject, where the measuring capacitor and the reference capacitor are connected in series with respect to each other, and jointly form a capacitive voltage divider, where the measuring capacitor and the reference capacitor do not relevantly influence the basic frequency and the signal shape of the applied alternating signals, tapping an electric signal from the measuring capacitor, and detecting at least one electric measuring variable of the electric signal, wherein
  at least one of the basic frequency and the signal shape of the applied alternating signals are changed, and
  at least one of the phase position and the amplitude of the applied alternating signals are changed.

9. A method according to claim 8, further comprising demodulating the electrical signal tapped from the measuring capacitor for detecting the at least one electric measuring variable, in that it is multiplied with an alternating signal.

* * * * *